US 011421168B2

(12) United States Patent
Henstock et al.

(10) Patent No.: US 11,421,168 B2
(45) Date of Patent: *Aug. 23, 2022

(54) METHODS FOR PREPARING FUEL ADDITIVES

(71) Applicant: BP OIL INTERNATIONAL LIMITED, Middlesex (GB)

(72) Inventors: Vince Henstock, London (GB); Brian Hill, London (GB); Sorin Vasile Filip, Reading (GB)

(73) Assignee: BP OIL INTERNATIONAL LIMITED, Sunbury on Thames (GB)

( * ) Notice: Subject to any disclaimer, the term of this patent is extended or adjusted under 35 U.S.C. 154(b) by 16 days.

This patent is subject to a terminal disclaimer.

(21) Appl. No.: 16/958,731

(22) PCT Filed: Dec. 19, 2018

(86) PCT No.: PCT/EP2018/086023
§ 371 (c)(1),
(2) Date: Jun. 28, 2020

(87) PCT Pub. No.: WO2019/129589
PCT Pub. Date: Jul. 4, 2019

(65) Prior Publication Data
US 2020/0332209 A1 Oct. 22, 2020

(30) Foreign Application Priority Data
Dec. 27, 2017 (GB) ...................... 1721960

(51) Int. Cl.
*C10L 1/24* (2006.01)
*C10L 1/233* (2006.01)
(Continued)

(52) U.S. Cl.
CPC ............ *C10L 1/233* (2013.01); *C07D 265/36* (2013.01); *C10L 10/10* (2013.01); *C10L 2270/023* (2013.01)

(58) Field of Classification Search
CPC .... C10L 1/233; C10L 10/10; C10L 2270/023; C10L 1/232; C07D 265/36
(Continued)

(56) References Cited

U.S. PATENT DOCUMENTS 4,288,589 A 9/1981 Loew et al.
4,861,914 A 8/1989 Weidig et al.
(Continued)

FOREIGN PATENT DOCUMENTS

CN 105272904 A 4/2019
EP 2172453 A1 4/2010
(Continued)

OTHER PUBLICATIONS

Perry, B. et al. "Achieving multi-isofrom-PI3K inhibition in a series of substituted 3,4-dihydro-2H-benzo[1,4]oxazines." Bioorg Med Chem Lett. 2008, 18, 16, p. 4700-4704.
(Continued)

*Primary Examiner* — Prem C Singh
*Assistant Examiner* — Francis C Campanell
(74) *Attorney, Agent, or Firm* — McDonnell Boehnen Hulbert & Berghoff LLP

(57) ABSTRACT

An optimised method for preparing a fuel additive f is provided. The method comprises carrying out the following reaction: (c, d, e) Starting material c may be prepared using an optimised method which comprises carrying out the following reaction: (a, b, c)

(Continued)

-continued

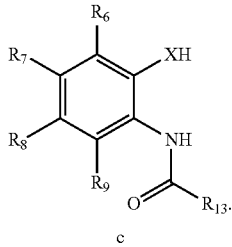

18 Claims, No Drawings

(51) Int. Cl.
    *C07D 265/36* (2006.01)
    *C10L 10/10* (2006.01)
(58) Field of Classification Search
    USPC .......................................................... 44/334
    See application file for complete search history.

(56) References Cited

U.S. PATENT DOCUMENTS

| 8,222,417 | B2 | 7/2012 | Suzuki et al. |
| 2005/0261244 | A1 | 11/2005 | Tuerdi et al. |
| 2006/0075680 | A1* | 4/2006 | Tort ........................ C10L 1/328 44/301 |
| 2006/0123696 | A1 | 6/2006 | Gaughan et al. |
| 2008/0064871 | A1 | 3/2008 | Hirata et al. |
| 2009/0094887 | A1 | 4/2009 | Calvert et al. |

FOREIGN PATENT DOCUMENTS

| EP | 3205701 A1 | 8/2017 |
| EP | 3205703 A1 | 8/2017 |
| GB | 1967-04506 G * | 12/1965 |
| GB | 2026524 A | 2/1980 |
| JP | H04247017 A | 9/1992 |
| KR | 20120102381 A | 9/2012 |
| WO | 2009001817 A1 | 12/2008 |
| WO | 2011048112 A1 | 4/2011 |
| WO | 2011103460 A1 | 8/2011 |
| WO | 2012009678 A1 | 1/2012 |
| WO | 2014047390 A1 | 3/2014 |
| WO | 2015063694 A1 | 5/2015 |
| WO | 2017108723 A2 | 6/2017 |
| WO | 2017137518 A1 | 8/2017 |
| WO | 2017142833 A1 | 8/2017 |

OTHER PUBLICATIONS

Dugar, S. et al. "A Concise and Efficient Synthesis of Substituted Morpholines." Synthesis. 2014, 47, 5, p. 712-720.
International Search Report and Written Opinion of International Application No. PCT/EP2018/086022, dated Apr. 10, 2019.
Coudert, G. et al. "A new synthesis of 3,4-dihydro-2H-1,4-benzoxazines using solid-liquid phase-transfer catalysis." Synthesis Georg Thieme Verlag. 1979, 7, p. 541-543.
Kotha, S. "Synthesis and Reactions of 3,4-dihydro-2H-1,4-benzoxazine Derivatives." Heterocycles. 1994, 38, p. 5-8.
Hernandez-Olmos, V. et al. "N-Substituted Phenoxazine and Acridone Derivatives: Structure-Activity Relationships of Potent P2X4 Receptor Antagonists." J. Med. Chem. 2012, 55, 22, p. 9576-9588.
Bunce, R.A. et al. "Tetrahydro-1,5-benzoxazepines and tetrahydro-1H-1,5-benzodiazepines by a tandem reduction-reductive amination reaction." J. Heterocyclic Chem. 2004, 41, 6, p. 963-970.
Shadyro, O.I. et al. "Synthesis and Antiviral Activity of N-Acyl Derivatives of 4,6-Di-(tert-butyl)-2-aminophenol." Pharmaceutical Chemistry Journal. 2003, 37, p. 399-401.
International Search Report and Written Opinion for International Application No. PCT/EP2018/086023, dated Jul. 4, 2019.
International Search Report and Written Opinion for International Application No. PCT/EP2018/086027, dated May 10, 2019.
Filippou, P.S. et al. "Regulation of the *Escherichia coli* AtoSC two component system by synthetic biologically active 6;7;8-trimethyl-1;4-benzoxazine analogues." Bioorgan Med Chem. 2011, 19, 16, p. 5061-5070.
Ramesh, C. et al. "A simple and facile route for the synthesis of 2H-1,4-benzoxazin-3-(4H)-ones via reductive cyclization of 2-(2-nitrophenoxy)acetonitrile adducts in the presence of Fe/acetic acid." Tetrahedron. 2011, 67, 6, p. 1187-1192.
Reddy, Ch. R. et al. "Reductive N-alkylation of aromatic amines and nitro compounds with nitriles using polymethylhydrosiloxane." Tetrahedron Let. 2007, 48, 15, p. 2765-2768.
International Search Report and Written Opinion for International Application No. PCT/EP2018/086025, dated Jun. 6, 2019.
Bartsch, H. et al. "Synthese und Reaktivität von 2- und 3-hydroxylierten Dihydro-1,4-Benzoxazinen." Monatshefte für Chemie. 1997, 110, p. 267-278.
Mizar, P. et al. "Synthesis of substituted 4-(3-alkyl-1,2,4-oxadiazol-5-ylmethyl)-3,4-dihydro-2H-1,4-benzoxazines and 4-(1H-benzimidazol-2-ylmethyl)-3,4-dihydro-2H-1,4-benzoxazines." Tetrahedron Let. 2006, 47, 44, p. 7823-7826.
Fu, Y. et al. "Simple and efficient synthesis of novel N-dichloroacetyl-3,4-dihydro-2H-1,4-benzoxazines." Heterocycl Commun. 2012, 18, 3, p. 143-146.
International Search Report and Written Opinion for International Application No. PCT/EP2018/086024, dated Jun. 6, 2019.
Knorr, L. "Synthesen in der »Oxazinreihe«." Ber. Dtsch. Chem. Ges. 1889, 22, p. 2081-2099.
Calderone, V. et al "Structural modifications of benzanilide derivatives, effictive potassium channel openers. X." Eur. J. Med. Chem. 2006, 41(12), p. 1421-1429.
Liu, Y. et al. "Concise synthesis of 3,4-dihydro-1,4-benzoxazines by three-component reactions of acyl chlorides, o-aminophenols and 1,2-dichloroethane." Tetrahedron. 2018, 74(27), p. 3691-3696.
Huerta, G. et al. "Facile Synthesis of Aminoalcohols by Ring Opening of Epoxides Under Solvent Free Conditions." Synthetic Commun. 2004, 34(13), p. 2393-2406.
Woydowski, K. "Optically Active Heterocycles through Ring Transformations on Oxirane3-carboxylate Derivatives." Sel. Org. React. Database (SORD). 1999. See CASREACT abstract accession No. 161:698073.
Gao, S. et al. "Synthesis and crystal structure of N-dichloroacetyl-3,4-dihydro-3-methyl-6-chloro-2H-1,4-benzoxazine". Journal of Chemistry. 2015, 2015, Article ID 268306, p. 1-5.
Yang, J. et al. "Synthesis, anti-cancer evaluation of benzenesulfoamide derivates as potent tubulin-targeting agents." Eur. J. Med. Chem. 2016, 122, p. 488-496.
Shadyro, O.I. et al. "Synthesis and Antiviral Activity of N-Acyl Derivatives of 4,6-Di-(tert-butyl)-2-aminophenol." Pharmaceutical Chemistry Journal. 2002, 36(8), p. 410-412.

* cited by examiner

METHODS FOR PREPARING FUEL ADDITIVES

This application is a national stage application under 35 U.S.C. § 371 of International Application No. PCT/EP2018/086023, filed Dec. 19, 2018, which claims priority to Great Britain Application No. 1721960.1, filed Dec. 27, 2017, the disclosures of which are explicitly incorporated by reference herein.

FIELD OF THE INVENTION

This invention relates to methods for preparing octane-boosting additives for use in a fuel for a spark-ignition internal combustion engine. In particular, the invention relates to methods for preparing octane-boosting fuel additives that are derivatives of benzo[1,4]oxazines and 1,5-benzoxazepines. The invention further relates to methods for preparing fuels for a spark-ignition internal combustion engine comprising the fuel additives.

BACKGROUND OF THE INVENTION

Spark-ignition internal combustion engines are widely used for power, both domestically and in industry. For instance, spark-ignition internal combustion engines are commonly used to power vehicles, such as passenger cars, in the automotive industry.

Fuels for a spark-ignition internal combustion engine (generally gasoline fuels) typically contain a number of additives to improve the properties of the fuel.

One class of fuel additives is octane improving additives. These additives increase the octane number of the fuel which is desirable for combatting problems associated with pre-ignition, such as knocking. Additisation of a fuel with an octane improver may be carried out by refineries or other suppliers, e.g. fuel terminals or bulk fuel blenders, so that the fuel meets applicable fuel specifications when the base fuel octane number is otherwise too low.

Organometallic compounds, comprising e.g. iron, lead or manganese, are well-known octane improvers, with tetraethyl lead (TEL) having been extensively used as a highly effective octane improver. However, TEL and other organometallic compounds are generally now only used in fuels in small amounts, if at all, as they can be toxic, damaging to the engine and damaging to the environment.

Octane improvers which are not based on metals include oxygenates (e.g. ethers and alcohols) and aromatic amines. However, these additives also suffer from various drawbacks. For instance, N-methyl aniline (NMA), an aromatic amine, must be used at a relatively high treat rate (1.5 to 2% weight additive/weight base fuel) to have a significant effect on the octane number of the fuel. NMA can also be toxic. Oxygenates give a reduction in energy density in the fuel and, as with NMA, have to be added at high treat rates, potentially causing compatibility problems with fuel storage, fuel lines, seals and other engine components.

Recently, a new class of octane-boosting additive has been discovered. These octane-boosting additives are derivatives of benzo[1,4]oxazines and 1,5-benzoxazepine, and show great promise due to their non-metallic nature, their low oxygenate content, and their efficacy at low treat rates (see WO 2017/137518).

Synthesis routes currently reported in the literature provide various descriptions of how benzoxazines may be prepared on a relatively small scale (hundreds of mg to up to 100 kg scale). For example, US 2008/064871—which relates to compounds for the treatment or prophylaxis of diseases relating to uric acid, such as gout—discloses the preparation of benzoxazine-derived compounds. Synthesis routes are also disclosed in Hernandez-Olmos et al: N-Substituted Phenoxazine and Acridone Derivatives: Structure-Activity Relationships of Potent P2X4 Receptor Antagonists (J. Med. Chem, 2012, 55 (22), 9576-9588).

However, there is a need for a method which is suitable for production of the new class of octane-boosting additives on an industrial scale, e.g. in an amount of from 50 to 20,000 tonnes per year. With production on this scale, it is highly desirable for any synthesis method to be optimised. This is particularly the case when relatively expensive starting materials, such as amino phenols, are used in the process.

Accordingly, there is a need for optimised methods for synthesising the new class of octane-boosting additives which are preferably suitable for implementation on a large scale.

SUMMARY OF THE INVENTION

Preparation Methods

The present invention provides a method for preparing a fuel additive f having the formula:

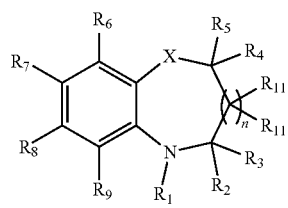

where: $R_1$ is hydrogen;

$R_2$, $R_3$, $R_4$, $R_5$, $R_{11}$ and $R_{12}$ are each independently selected from hydrogen, alkyl, alkoxy, alkoxy-alkyl, secondary amine and tertiary amine groups;

$R_6$, $R_7$, $R_8$ and $R_9$ are each independently selected from hydrogen, alkyl, alkoxy, alkoxy-alkyl, secondary amine and tertiary amine groups;

X is selected from —O— or —$NR_{10}$—, where $R_{10}$ is selected from hydrogen and alkyl groups; and n is 0 or 1.

The method comprises carrying out the following reaction:

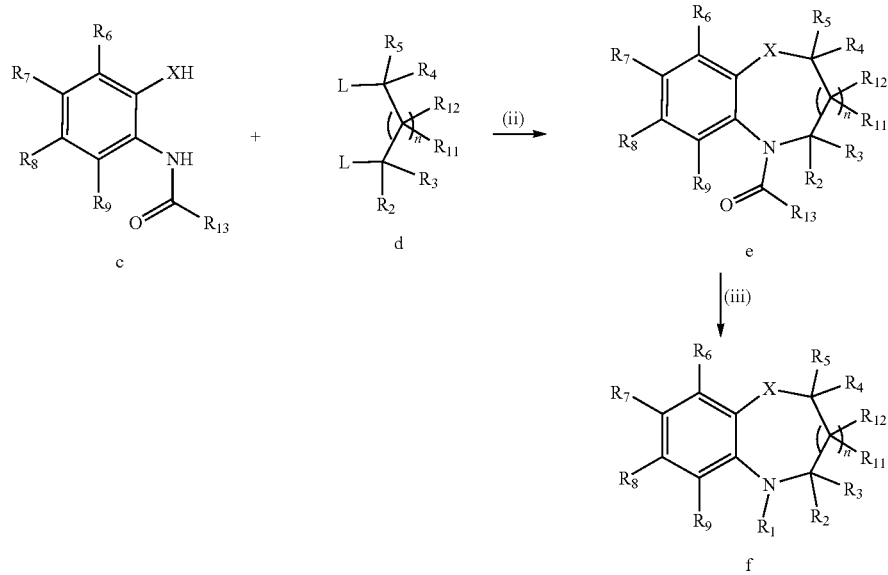

where: $R_{13}$ is selected from alkyl and aryl groups; and
each L is independently selected from leaving groups, and wherein step (ii) is conducted in the presence of a base selected from alkali metal hydroxides and alkali metal carbonates, and wherein the base is used in an amount of at least 2 molar equivalents as compared to starting material c.

The present invention also provides a method for preparing a starting material c, said method comprising carrying out the following reaction:

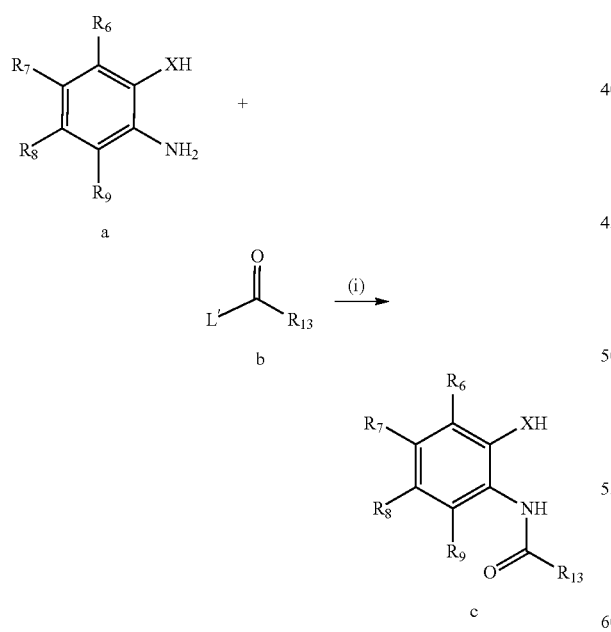

where: L' is a leaving group, and
wherein step (i) is carried out in the presence of a solvent system which comprises a primary solvent, the primary solvent selected from tetrahydrofuran and dichloromethane.

Also provided is a fuel additive f which is obtainable by a method of the present invention.

The present invention further provides a process for preparing a fuel for a spark-ignition internal combustion engine, said process comprising blending an additive composition of the present invention (comprising f) with a base fuel. Said process may therefore comprise:

preparing a fuel additive f using a method of the present invention; and
blending the fuel additive with a base fuel.

A fuel for a spark-ignition internal combustion engine is also provided. The fuel comprises a fuel additive f of the present invention and a base fuel.

DETAILED DESCRIPTION OF THE INVENTION

The present invention provides a method for preparing a fuel additive f, as well as a method for providing a starting material c for use in the method of preparing the fuel additive f.

The starting material c is prepared by a method which comprises carrying out the following reaction:

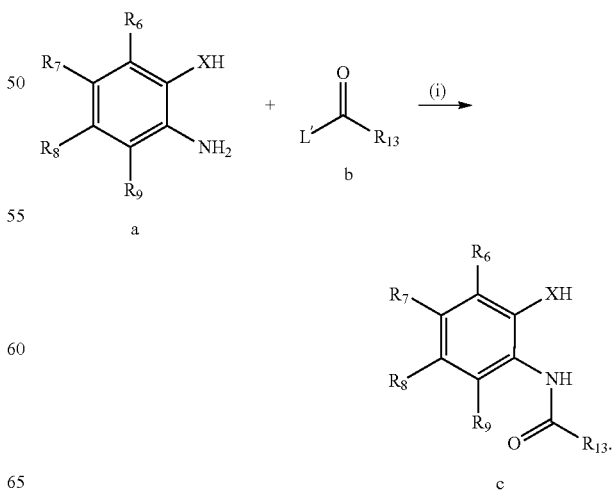

Step (i) of the method is carried out in the presence of a solvent system which comprises a primary solvent, the primary solvent selected from tetrahydrofuran and dichloromethane. These solvents are preferred since their use leads to the production of starting material c in high yields with good purity. Dichloromethane is particularly preferred as the solvent, giving starting material c with high purity.

The solvent system preferably comprises at least 30%, and preferably at least 40%, by volume of the primary solvent.

In preferred embodiments, the solvent system further comprises water, preferably in an amount of at least 30%, and more preferably at least 40%, by volume.

Generally, at least 90%, preferably at least 95%, and more preferably at least 99%, by volume of the solvent system is made up of the primary solvent and, if present, water.

The solvent system may be used in an amount of from 5 to 15 ml/g, preferably from 6 to 10 mg/g, and more preferably from 6.5 to 8.5 ml/g, of reagent a.

Reagent b is used in step (i) in an amount of from 1 to 1.05 molar equivalents, preferably from 1.0005 to 1.01 molar equivalents, and more preferably from 1.001 to 1.005 molar equivalents as compared to reagent a.

Step (i) is preferably conducted in the in the presence of a base, and more preferably a carbonate base. The carbonate base is preferably an alkali metal carbonate and may be selected from sodium carbonate, potassium carbonate, sodium bicarbonate, potassium bicarbonate and caesium carbonate, and still more preferably is sodium bicarbonate.

The base in step (i) is preferably used in an amount of 0.8 to 2 molar equivalents, preferably from 1 to 1.5 molar equivalents, and more preferably from 1.05 to 1.2 molar equivalents as compared to reagent a.

Step (i) may conveniently be carried out at room temperature (e.g. at a temperature of from 15 to 30° C., preferably from 20 to 25° C.), or with cooling (e.g. to a temperature of from 5 to 15° C.).

Step (i) is preferably conducted at ambient pressure, i.e. a pressure of approximately 1 bar.

The reaction is preferably carried out for at least 30 minutes, preferably at least an hour, and more preferably at least four hours.

Reagent b contains a leaving group, L'. This group is preferably selected from: halides (e.g. Cl, Br, I), substituted aryloxy groups (e.g. —O—Ar, where Ar selected from nitro-substituted aryl groups such as p-nitrophenyl) and sulfonates (e.g. —OSO$_2$A, where A is selected from tolyl, methyl, —CF$_3$, —CH$_2$Cl, phenyl and p-nitrophenyl), more preferably from halides, and still more preferably from Cl and Br.

Reagent b also contains substituent $R_{13}$. This group is selected from alkyl and aryl groups. $R_{13}$ is preferably selected from methyl, ethyl and phenyl. More preferably, $R_{13}$ is phenyl. This is because a phenyl substituent is more easily removed in step (iii) of the method, and can be readily separated from product f, which is an oil, by washing with water.

The methods of the present invention may be used to prepare starting material c at a yield of greater than 85%, more preferably greater than 90%, and still more preferably greater than 95%. As is conventional in the art, the yield (as with all yields mentioned herein) is calculated based on the amount of experimentally produced product as compared to the theoretical amount of product that would be expected based on the stoichiometry of the reaction.

The methods of the present invention may be used to prepare starting material c in a form having a purity of greater than 97%, preferably greater than 98%, and more preferably greater than 99% by weight. Purity may be measured using LCMS, with the ratio of starting material c peak area to total peak area in the chromatogram assumed to equal the ratio by weight. LCMS may be carried out using the conditions detailed in the Examples.

Once starting material c has been prepared, it may be used in a method for preparing an octane-boosting fuel additive f.

The method for preparing an octane-boosting fuel additive f comprises two steps: steps (ii) and (iii). In step (ii) of the method, a ring closing reaction is carried out in which intermediate e is formed:

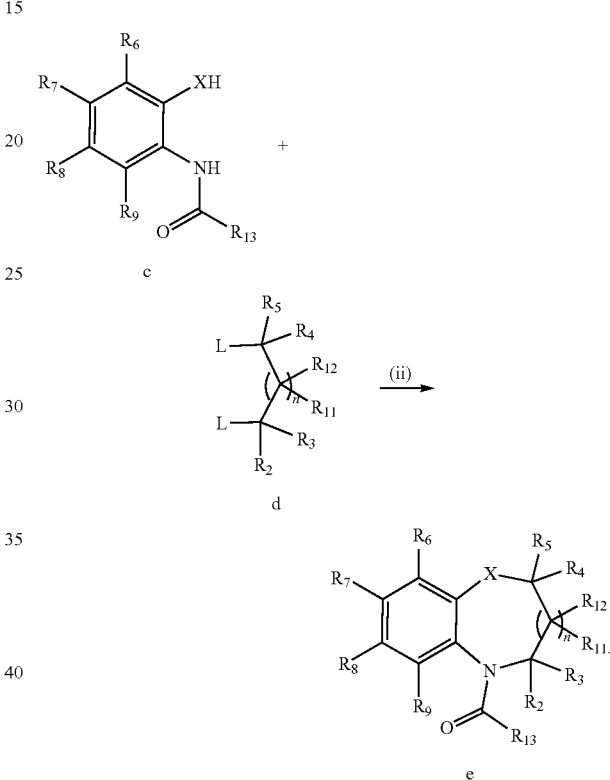

Whilst starting material c is preferably prepared using a method of the present invention, it may also be obtained by other means.

Step (ii) of the method is conducted in the presence of a base selected from alkali metal hydroxides and alkali metal carbonates. The use of these bases encourages the formation of intermediate e.

The use of alkali metal hydroxides is particularly preferred. The alkali metal hydroxide may be selected from sodium hydroxide and potassium hydroxide. Sodium hydroxide is particularly preferred.

The carbonate base may be selected from sodium carbonate, potassium carbonate, sodium bicarbonate, potassium bicarbonate and caesium carbonate. Caesium carbonate is preferred.

Sodium hydroxide and caesium carbonate are particularly preferred, since they reduce the formation of the following dimer by-product:

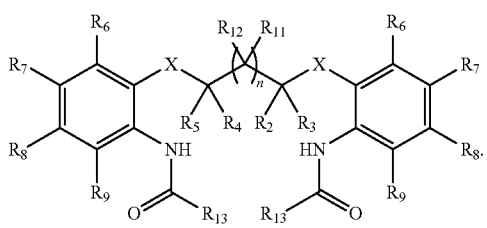

The base is used in step (ii) an amount of at least 2 molar equivalents as compared to starting material c. Preferably, the base is used in an amount of from 2 to 12 molar equivalents, preferably from 3 to 10 molar equivalents, and more preferably from 4 to 8 molar equivalents as compared to starting material c.

In some embodiments, particularly where the base is an alkali metal hydroxide, the base is added to the starting material c in at least two portions, for instance in two or three portions, and preferably in two portions. Preferably, no more than 70%, more preferably no more than 60%, and still more preferably no more than 55% of the total amount of base used is added to the starting material c in each portion.

The time interval between the addition of each portion may be at least an hour, preferably at least 2 hours, and more preferably at least 3 hours. Typically the time interval will be less than 6 hours.

Each portion may be added dropwise (e.g. over a period of from 15 minutes to 1 hour), though it is generally preferred for each portion to be added in one go. It will be appreciated, that where each portion of the base is added dropwise, the time interval between the addition of each portion is taken to be the time interval between the first drops that are added from each portion.

Reagent d is preferably used in step (ii) an amount of from 1 to 20 molar equivalents, preferably from 2 to 15 molar requivalents, and more preferably from 4 to 10 molar equivalents as compared to starting material c.

Step (ii) is preferably conducted in the presence of a solvent selected from methyl isobutyl ketone and acetonitrile. Acetonitrile is particularly preferred.

Preferably the solvent is used in an amount of at least 10 ml/1 g of starting material c.

In some embodiments, step (ii) is conducted in the presence of a catalyst, preferably a tetrabutylammonium halide, and more preferably tetrabutylammonium bromide.

The catalyst may be used in an amount of less than 1 molar equivalent, preferably less than 0.5 molar equivalents, and more preferably less than 0.1 molar equivalents as compared to starting material c.

Step (ii) may be conducted at a temperature of from 10 to 150° C.

Where the base used in step (ii) is an alkali metal carbonate, the reaction is preferably conducted at an elevated temperature, e.g. at a temperature of at least 30° C., preferably at least 50° C., and more preferably at least 60° C. In some embodiments, the reaction in step (ii) may be conducted under reflux. Elevated temperatures are preferred to reduce by-product formation.

Where the base used in step (ii) is an alkali metal hydroxide, the reaction is preferably conducted at a temperature of from 15 to 40° C., preferably from 20 to 35° C. and more preferably from 22 to 30° C.

The reaction in step (ii) may be carried out for at least 12 hours, and preferably at least 15 hours.

Step (ii) is preferably conducted at ambient pressure, i.e. a pressure of approximately 1 bar.

In preferred embodiments, step (ii) is carried out as a single reaction (i.e. with one set of reagents and under one set of conditions). However, in some embodiments, step (ii) comprises the following sub-steps:

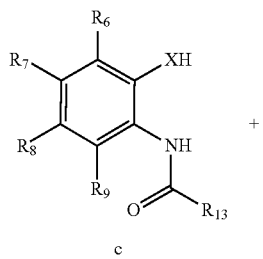

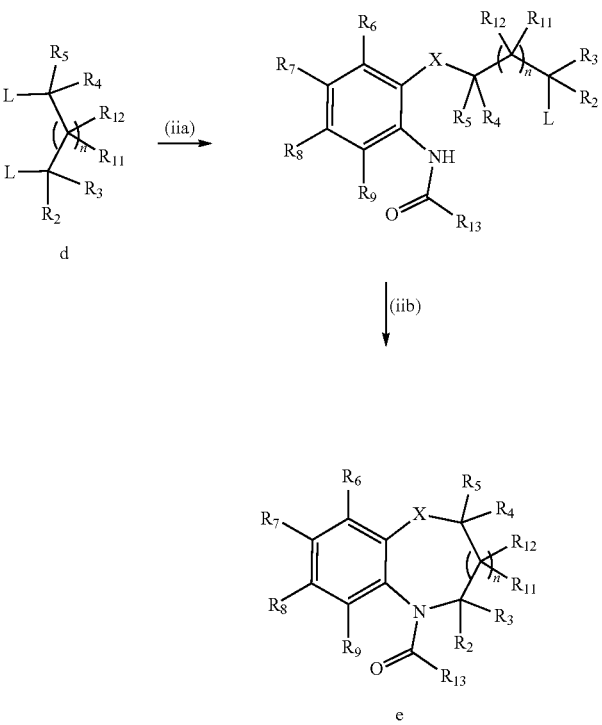

It will be appreciated that, in some instances, step (iib) will occur spontaneously on formation of the alkylated phenol intermediate. For the purposes of the present invention, these instances are considered to be embodiments in which step (ii) is carried out as a single reaction.

Conditions for step (iia) are preferably as described above for step (ii). However, where ring closing does not occur spontaneously in step (iib), different conditions may be used to carry out step (iib).

For instance, step (iib) may be carried out in the presence of a base, such as a base selected from alkali metal hydrides (e.g. sodium hydride), carbonates (e.g. alkali metal carbonates such as sodium carbonate, sodium bicarbonate, potassium carbonate and potassium bicarbonate) and an alkali metal alkoxide (e.g. alkali metal tert-butoxides such as sodium tert-butoxide or potassium tert-butoxide).

Solvents for use in step (iib) may be selected from aprotic solvents, such as tetrahydrofuran, acetonitrile, dimethoxyethane, dioxane, N-methyl-2-pyrrolidone, dimethylformamide, dimethylacetamide, dimethyl sulfoxide, ethylene carbonate, sulfolane, diphenyl ether, acetonitrile, 2-nitropropane, acetone, butan-2-one, butylformate, ethyl acetate, isobutyronitrile, methylacetate, methyformate, nitromethane, oxolane and propionitrile, and preferably from dimethylformamide, N-methyl-2-pyrrolidone, dimethylacetamide, dimethyl sulfozide and sulfolane. Aprotic solvents are well-known in the art as solvents which are not capable of donating protons. Aprotic solvents do not contain hydrogen atoms bound to a nitrogen or an oxygen.

During step (ii), the leaving groups L are lost from reagent d. Preferably, each L is independently selected from: halides (e.g. Cl, Br, I), substituted aryloxy groups (e.g. —O—Ar, where Ar selected from nitro-substituted aryl groups such as p-nitrophenyl) and sulfonates (e.g. —OSO$_2$A, where A is selected from tolyl, methyl, —CF$_3$, —CH$_2$Cl, phenyl and p-nitrophenyl), more preferably from halides, and still more preferably from Cl and Br.

Preferably, at least one and, more preferably, each L is Br. This is particularly the case where the base is an alkali metal hydroxide. Where each L is Cl, then step (ii) is preferably conducted in the presence of a catalyst, e.g. a tetrabutylammonium halide as mentioned above.

The methods of the present invention may be used to prepare intermediate e in a yield of greater than 60%, more preferably greater than 70%, and more preferably greater than 80%.

The methods of the present invention may be used to prepare intermediate e in a form having a purity of greater than 80%, preferably greater than 85%, and more preferably greater than 90% by weight. Purity may be measured using LCMS, with the ratio of intermediate e peak area to total peak area in the chromatogram assumed to equal the ratio by weight.

The dimer by-product may be formed in an amount of less than 20%, preferably less than 15%, and more preferably less than 10% by weight of intermediate e. The % by weight of dimer by-product may be measured using LCMS, with the ratio of dimer by-product peak area to intermediate e peak area in the chromatogram assumed to equal the ratio by weight.

As mentioned above, LCMS may be carried out using the conditions detailed in the Examples.

In step (iii) of the method, the nitrogen group of intermediate e is deprotected, thereby forming product f.

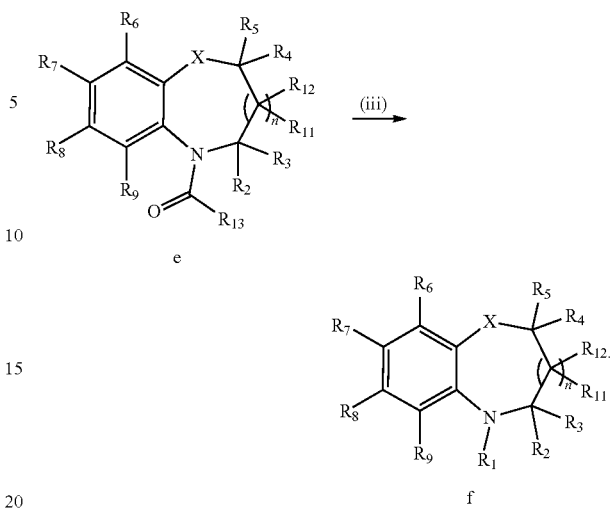

Conventional deprotection methods may be used. However, in preferred embodiments, step (iii) is preferably carried out in an aqueous solution, preferably comprising an acid or a base, and more preferably comprising a base.

The base is preferably selected from inorganic bases, such as from alkali metal bases, preferably from alkali metal hydroxides, and more preferably is sodium hydroxide.

The base is preferably used in step (iii) in a molar excess as compared to intermediate e. For example, the base may be used in an amount of at least twice, and preferably at least three time the molar quantity of intermediate e. This is believed to help to remove the dimer by-product.

The acid is preferably selected from inorganic acids, and more preferably is hydrochloric acid.

Step (iii) may conducted at an elevated temperature, e.g. at a temperature of at least 30° C., preferably at least 50° C., and more preferably at least 60° C. In some embodiments, the reaction in step (iii) may be conducted under reflux.

The reaction in step (iii) may be carried out for at least 12 hours, and preferably at least 15 hours.

Step (iii) is preferably conducted at ambient pressure, i.e. a pressure of approximately 1 bar.

In a very specific embodiment, step (i) is carried out in the presence of a base (e.g. sodium bircarbonate) and a solvent (e.g. dichloromethane); step (ii) is carried out in the presence of a base (e.g. sodium hydroxide) and a solvent (e.g. acetonitrile) and step (iii) is carried out in the presence of an aqueous base (e.g. sodium hydroxide).

The methods of the present invention are preferably carried out on an industrial scale. For instance, where the method of preparing fuel additive f is a batch process, the fuel additive is preferably produced in a batch quantity of greater than 100 kg, preferably greater than 150 kg, and more preferably greater than 200 kg. The method may also be carried out as a continuous process.

In order to produce the fuel additive on an industrial scale, steps (i), (ii) and (iii) are preferably carried out in reactors having a capacity of at least 500 L, preferably at least 750 L, and more preferably at least 1000 L. It will be appreciated that more than one (e.g. each) step may be carried out in the same reactor.

Octane-Boosting Additive f

Fuel additives f that are prepared using the methods of the present invention have the following formula:

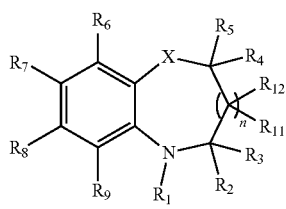

where: $R_1$ is hydrogen;
$R_2$, $R_3$, $R_4$, $R_5$, $R_{11}$ and $R_{12}$ are each independently selected from hydrogen, alkyl, alkoxy, alkoxy-alkyl, secondary amine and tertiary amine groups;
$R_6$, $R_7$, $R_8$ and $R_9$ are each independently selected from hydrogen, alkyl, alkoxy, alkoxy-alkyl, secondary amine and tertiary amine groups;
X is selected from —O— or —$NR_{10}$—, where $R_{10}$ is selected from hydrogen and alkyl groups; and
n is 0 or 1.

Preferred substituents for the fuel additive f are described below. It will be appreciated that the preferred substitution patterns also apply to the starting material c, and reagents a and b from which starting material c is prepared, as well as reagent d and intermediate e from which the fuel additive f is prepared.

In some embodiments, $R_2$, $R_3$, $R_4$, $R_5$, $R_{11}$ and $R_{12}$ are each independently selected from hydrogen and alkyl groups, and preferably from hydrogen, methyl, ethyl, propyl and butyl groups. More preferably, $R_2$, $R_3$, $R_4$, $R_5$, $R_{11}$ and $R_{12}$ are each independently selected from hydrogen, methyl and ethyl, and even more preferably from hydrogen and methyl.

In some embodiments, $R_6$, $R_7$, $R_8$ and $R_9$ are each independently selected from hydrogen, alkyl and alkoxy groups, and preferably from hydrogen, methyl, ethyl, propyl, butyl, methoxy, ethoxy and propoxy groups. More preferably, $R_6$, $R_7$, $R_8$ and $R_9$ are each independently selected from hydrogen, methyl, ethyl and methoxy, and even more preferably from hydrogen, methyl and methoxy.

Advantageously, at least one of $R_2$, $R_3$, $R_4$, $R_5$, $R_6$, $R_7$, $R_8$, $R_9$, $R_{11}$ and $R_{12}$, and preferably at least one of $R_6$, $R_7$, $R_8$ and $R_9$, is selected from a group other than hydrogen. More preferably, at least one of $R_7$ and $R_8$ is selected from a group other than hydrogen. Alternatively stated, the fuel additive may be substituted in at least one of the positions represented by $R_2$, $R_3$, $R_4$, $R_5$, $R_6$, $R_7$, $R_8$, $R_9$, $R_{11}$ and $R_{12}$, preferably in at least one of the positions represented by $R_6$, $R_7$, $R_8$ and $R_9$, and more preferably in at least one of the positions represented by $R_7$ and $R_8$. It is believed that the presence of at least one group other than hydrogen may improve the solubility of the octane-boosting fuel additives f in a fuel.

Also advantageously, no more than five, preferably no more than three, and more preferably no more than two, of $R_2$, $R_3$, $R_4$, $R_5$, $R_6$, $R_7$, $R_8$, $R_9$, $R_{11}$ and $R_{12}$ are selected from a group other than hydrogen. Preferably, one or two of $R_2$, $R_3$, $R_4$, $R_5$, $R_6$, $R_7$, $R_8$, $R_9$, $R_{11}$ and $R_{12}$ are selected from a group other than hydrogen. In some embodiments, only one of $R_2$, $R_3$, $R_4$, $R_5$, $R_6$, $R_7$, $R_8$, $R_9$, $R_{11}$ and $R_{12}$ is selected from a group other than hydrogen.

It is also preferred that at least one of $R_2$ and $R_3$ is hydrogen, and more preferred that both of $R_2$ and $R_3$ are hydrogen.

In preferred embodiments, at least one of $R_4$, $R_5$, $R_7$ and $R_8$ is selected from methyl, ethyl, propyl and butyl groups and the remainder of $R_2$, $R_3$, $R_4$, $R_5$, $R_6$, $R_7$, $R_8$, $R_9$, $R_{11}$ and $R_{12}$ are hydrogen. More preferably, at least one of $R_7$ and $R_8$ are selected from methyl, ethyl, propyl and butyl groups and the remainder of $R_2$, $R_3$, $R_4$, $R_5$, $R_6$, $R_7$, $R_8$, $R_9$, $R_{11}$ and $R_{12}$ are hydrogen.

In further preferred embodiments, at least one of $R_4$, $R_5$, $R_7$ and $R_8$ is a methyl group and the remainder of $R_2$, $R_3$, $R_4$, $R_5$, $R_6$, $R_7$, $R_8$, $R_9$, $R_{11}$ and $R_{12}$ are hydrogen. More preferably, at least one of $R_7$ and $R_8$ is a methyl group and the remainder of $R_2$, $R_3$, $R_4$, $R_5$, $R_6$, $R_7$, $R_8$, $R_9$, $R_{11}$ and $R_{12}$ are hydrogen.

Preferably, X is —O— or —$NR_{10}$—, where $R_{10}$ is selected from hydrogen, methyl, ethyl, propyl and butyl groups, and preferably from hydrogen, methyl and ethyl groups. More preferably, $R_{10}$ is hydrogen. In preferred embodiments, X is —O—.

n may be 0 or 1, though it is preferred that n is 0.

Octane-boosting fuel additives that may be used in the present invention include:

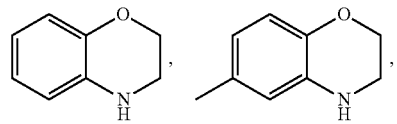

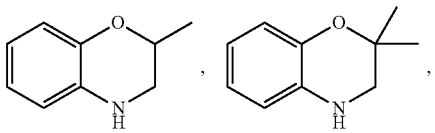

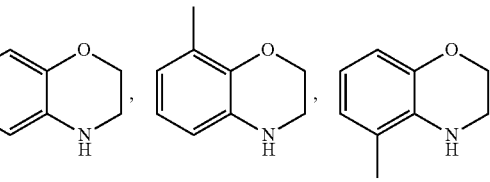

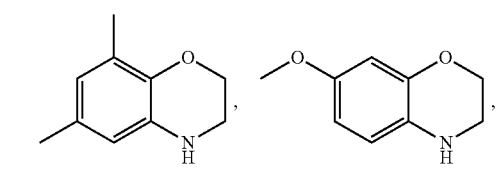

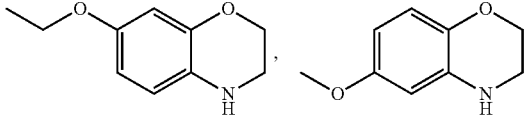

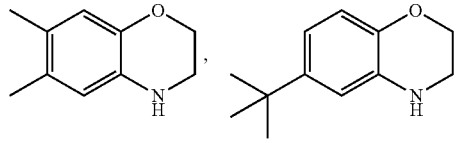

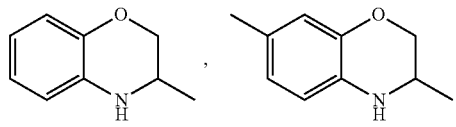

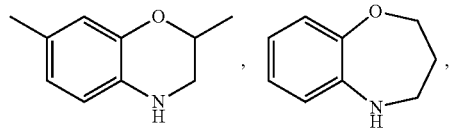

-continued

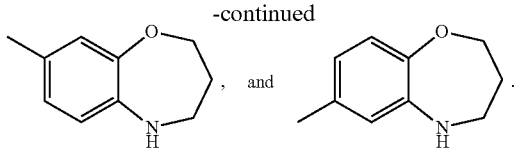

Preferred octane-boosting additives include:

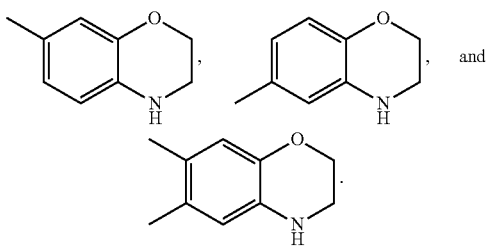

Particularly preferred is the octane-boosting additive:

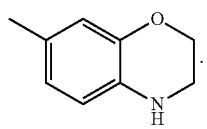

A mixture of fuel additives f may be used in the fuel composition. For instance, the fuel composition may comprise a mixture of:

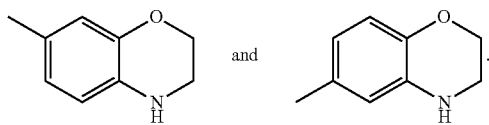

It will be appreciated that references to alkyl groups include different isomers of the alkyl group. For instance, references to propyl groups embrace n-propyl and i-propyl groups, and references to butyl embrace n-butyl, isobutyl, sec-butyl and tert-butyl groups.

Additive and Fuel Compositions

The present invention provides fuel additives f which are obtainable by a method according to the present invention. Preferably, the fuel additives are obtained by a method according to the present invention.

The present invention also provides a process for preparing a fuel for a spark-ignition internal combustion engine, said process comprising:

preparing a fuel additive f using a method of the present invention; and blending the fuel additive with a base fuel.

A fuel for a spark-ignition internal combustion engine is also provided. The fuel comprises a fuel additive f, obtainable and preferably obtained by a method according to the present invention, and a base fuel.

Gasoline fuels (including those containing oxygenates) are typically used in spark-ignition internal combustion engines. Commensurately, the fuel composition that may be prepared according to the process of the present invention may be a gasoline fuel composition.

The fuel composition may comprise a major amount (i.e. greater than 50% by weight) of liquid fuel ("base fuel") and a minor amount (i.e. less than 50% by weight) of additive composition of the present invention. Examples of suitable liquid fuels include hydrocarbon fuels, oxygenate fuels and combinations thereof.

The fuel composition may contain the octane-boosting fuel additive f in an amount of up to 20%, preferably from 0.1% to 10%, and more preferably from 0.2% to 5% weight additive/weight base fuel. Even more preferably, the fuel composition contains the fuel additive in an amount of from 0.25% to 2%, and even more preferably still from 0.3% to 1% weight additive/weight base fuel. It will be appreciated that, when more than one octane-boosting fuel additive f is used, these values refer to the total amount of fuel additive f in the fuel.

The fuel compositions may comprise at least one other further fuel additive. Examples of such other additives that may be present in the fuel compositions include detergents, friction modifiers/anti-wear additives, corrosion inhibitors, combustion modifiers, anti-oxidants, valve seat recession additives, dehazers/demulsifiers, dyes, markers, odorants, anti-static agents, anti-microbial agents, and lubricity improvers. Further octane improvers may also be used in the fuel composition, i.e. octane improvers which do not have the structure of octane-boosting fuel additive f.

The fuel compositions are used in a spark-ignition internal combustion engine. Examples of spark-ignition internal combustion engines include direct injection spark-ignition engines and port fuel injection spark-ignition engines. The spark-ignition internal combustion engine may be used in automotive applications, e.g. in a vehicle such as a passenger car.

The invention will now be described with reference to the following non-limiting examples.

EXAMPLES

LCMS analysis was carried out in the following examples using the conditions provided in the following table:

| Instrument: | Agilent 1260 infinity HPLC with Agilent 6130 single quadrupole mass spec |
| --- | --- |
| Column | Phenomenex Kinetex XB-$C_{18}$, 50 × 4.6 mm, 2.6 μm |
| Mobile phase: | A: 0.1% (v/v) formic acid in water<br>B: 100% acetonitrile |

| Gradient: | Time [min] | A [%] | B [%] |
| --- | --- | --- | --- |
| | 0 | 95 | 5 |
| | 1.37 | 2 | 98 |
| | 1.60 | 2 | 98 |
| | 1.83 | 95 | 5 |
| | 2.25 | 95 | 5 |

| Flow rate: | 2.0 mL/min |
| --- | --- |
| Flow rate: | 1.0 mL/min |
| Column temperature: | 40° C. |
| Injection volume: | 1 μL |
| Detection: | Wavelength 225 nm<br>Bandwidth 50 nm |
| Mass spec parameters: | Scanning in ES +/− & APCI over 70-1000 m/z |
| Needle wash: | MeOH |
| Sample preparation: | Solution prepared using 0.5-1.0 mg/ml acetonitrile or DMSO |

Example 1: Preparation of Starting Material c

A starting material c for use in the preparation of an octane-boosting fuel additive f was prepared according to the following scheme:

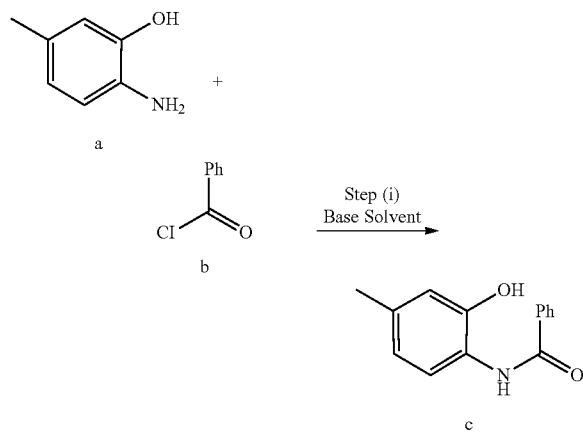

In a first experiment, 2-amino-5-methyl phenol (600 g; 1 eq) and sodium bicarbonate (451 g; 1.1 eq) in water (3 L) and dichloromethane (4 L) was added to a jacketed 10 L reactor with an anchor stirrer. A solution of benzoyl chloride (688.79 g; 1.005 eq) in dichloromethane (600 ml) was added, at 10° C., over 90 minutes, to the mixture giving a small exotherm (~3° C.). The reaction mixture (a suspension) was stirred at 10° C. for 24 hours. The solid was filtered off and washed with water (2×750 ml) and dichloromethane (2×500 ml)—which removes the red colour—leaving a beige solid. The solid was dried in vacuo at 50° C. Starting material c was obtained at a yield of 1016 g (91.7%) and a purity of 100% (measured with LCMS, (M+1)). NMR was also consistent with the target structure.

The experiment was repeated twice. The starting material c was obtained at a yield of 1021 g (92.2%) and a purity of 100% (measured with LCMS, (M+1)), and at a yield of of 1008 g (91.0%) and a purity of 100% (measured with LCMS, (M+1)).

In a second experiment, 2-amino-5-methyl phenol (1400 g; 1 eq) and sodium bicarbonate (1050 g: 1.1 eq) in water (7 L) and dichloromethane (4.5 L) was added to a jacketed 20 L reactor with a turbine stirrer. A solution of benzoyl chloride (1607.18 g; 1.005 eq) in dichloromethane (800 ml) was added, at 10° C., over 100 minutes, to the mixture giving a small exotherm (~3° C.). The reaction mixture (initially a suspension in an emulsion, but with time a biphasic mixture with suspended solids in the lower oily layer) was stirred at 10° C. for 24 hours. The solid was filtered off and washed with water (2×1000 ml) and dichloromethane (2×1000 ml)—which removes the red colour—leaving a beige solid. The solid was dried at 50° C. Starting material c was obtained at a yield of 2245 g (94.6%) and a purity of 99.7% (measured with LCMS, (M+1)). NMR was also consistent with the target structure.

In a third experiment, 2-amino-5-methyl phenol (100 g; 1 eq) and sodium bicarbonate (75 g: 1.1 eq) in water (250 ml) and dichloromethane (450 ml) was added to a reactor. A solution of benzoyl chloride (114.2 g; 1.005 eq) in dichloromethane (40 ml) was added to the mixture. The reaction mixture was stirred at room temperature for 23 hours. The solid was filtered off and washed with water (2×120 ml), dichloromethane (2×120 ml)—which removes the red colour, leaving a beige solid—and water (120 ml). The solid was dried at 50° C. Starting material c was obtained at a yield of 175 g (94.7%) and a purity of 100% (measured with LCMS, (M+1)). NMR was also consistent with the target structure.

The experiment was repeated on a larger scale. 2-amino-5-methyl phenol (2000 g; 1 eq) and sodium bicarbonate (1500 g: 1.1 eq) in water (5 L) and dichloromethane (8.5 L) was added to a reactor. A solution of benzoyl chloride (2295.98 g; 1.005 eq) in dichloromethane (700 ml) was added, at 10° C., over 3 hours, to the mixture. The reaction mixture was stirred at 10° C. for 23 hours. The solid was filtered off and washed with water (2×1500 ml) and dichloromethane (2×1500 ml)—which removes the red colour, to leave a beige solid—and water (1500 L). The solid was dried at 50° C. Starting material c was obtained at a yield of 3521 g (95%) and a purity of 100% (measured with LCMS, (M+1)). NMR was also consistent with the target structure.

Further experiments were carried out using similar methods, but under a variety of conditions in order to optimise the production of starting material c. The results are provided in the following table:

|   | Scale g (sm) | Primary solvent | ml/g | Other solvent | ml/g | Base | Reagent b eq. | Time | Yield | Purity |
|---|---|---|---|---|---|---|---|---|---|---|
| 1 | 100 | CH$_2$Cl$_2$ | 10 | — | — | NaHCO$_3$ | 1.05 | o/n | 85% | 100% |
| 2 | 100 | CH$_2$Cl$_2$ | 10 | — | — | NaHCO$_3$ | 1.05 | o/n | 81% | 100% |
| 3 | 100 | CH$_2$Cl$_2$ | 10 | Water | 5 | NaHCO$_3$ | 1.05 | o/n | 84% | 100% |
| 4 | 5 | Water | 40 | — | — | — | 1.1 | ¼ h | 61% | 82% |
| 5 | 5.2 | Water | 40 | — | — | NaHCO$_3$ | 1.02 + 0.5 | o/n | 82% | 98% |
| 6 | 20.8 | Water | 20 | CH$_2$Cl$_2$ | 1 | NaHCO$_3$ | 1.02 | ⅓ h | 91% | 8% a |
| 7 | 53 | Water | 9 | CH$_2$Cl$_2$ Hexane | 2 1 | NaHCO$_3$ | 1.1 | ⅓ h | 71% | 8% a |
| 8 | 20.2 | Water | 20 | CH$_2$Cl$_2$ | 1 | NaHCO$_3$ | 1.05 + 0.05 | ½ h | 88% | 4% a |
| 9 | 10.5 | CH$_2$Cl$_2$ | 8 | Water | 5 | NaHCO$_3$ | 1.01 | o/n | 86% | 100% |
| 10 | 10.1 | DMF | 10 | — | — | NaHCO$_3$ | 1.05 + 0.05 | 2 h | 55% | 99% |
| 11 | 10.1 | CH$_2$Cl$_2$ | 10 | — | — | Et$_3$N | 1.05 | ½ h | — | — |
| 12 | 5 | MeCN | 10 | — | — | NaHCO$_3$ | 1.05 | ½ h | 83% | 100% |
| 13 | 5 | MeCN | 10 | Water | 5 | NaHCO$_3$ | 1.05 | ½ h | 70% | 100% |
| 14 | 5 | THF | 10 | — | — | NaHCO$_3$ | 1.05 | ½ h | 97% | 96.1% |
| 15 | 10.5 | THF | 9.5 | Water | 2.4 | NaHCO$_3$ | 1.01 | ½ h | 99.6% | 97.7% |
| 16 | 10.5 | MeCN | 9.5 | Water | 10 | NaHCO$_3$ | 1.01 | ½ h | 87% | 100% |

| | Scale g (sm) | Primary solvent | ml/g | Other solvent | ml/g | Base | Reagent b eq. | Time | Yield | Purity |
|---|---|---|---|---|---|---|---|---|---|---|
| 17 | 21 | THF | 9.5 | Water | 2.4 | NaHCO$_3$ | 1.001 | 1 h | 98.6% | 99.6% |
| 18 | 100 | THF | 9.5 | Water | 2.4 | NaHCO$_3$ | 1.001 | 1 h | 99.5% | 98.3% |
| 19 | 600 | THF | 9.5 | Water | 2.4 | NaHCO$_3$ | 1.001 | 4 h | 99.7% | 99.0% |
| 20 | 600 | CH$_2$Cl$_2$ | 7.6 | Water | 5 | NaHCO$_3$ | 1.005 | o/n | 91.7% | 100% |
| 21 | 600 | CH$_2$Cl$_2$ | 7.6 | Water | 5 | NaHCO$_3$ | 1.005 | o/n | 92.2% | 100% |
| 22 | 600 | CH$_2$Cl$_2$ | 7.6 | Water | 5 | NaHCO$_3$ | 1.005 | o/n | 91% | 100% |
| 23 | 600 | CH$_2$Cl$_2$ | 7.6 | Water | 5 | NaHCO$_3$ | 1.005 | o/n | 93% | 100% |
| 24 | 600 | CH$_2$Cl$_2$ | 7.6 | Water | 5 | NaHCO$_3$ | 1.005 | o/n | 93% | 100% |
| 25 | 2 × 600 | CH$_2$Cl$_2$ | 7.6 | Water | 5 | NaHCO$_3$ | 1.005 | o/n | 92.5% | 100% |
| 26 | 2 × 600 | CH$_2$Cl$_2$ | 7.6 | Water | 5 | NaHCO$_3$ | 1.005 | o/n | 93% | 100% |
| 27 | 1200 | CH$_2$Cl$_2$ | 7.6 | Water | 5 | NaHCO$_3$ | 1.005 | o/n | 92.8% | 100% |
| 28 | 100 | CH$_2$Cl$_2$ | 3.25 | Water | 5 | NaHCO$_3$ | 1.005 | o/n | 93.3% | 99.7% |
| 29 | 1200 | CH$_2$Cl$_2$ | 7.6 | Water | 5 | NaHCO$_3$ | 1.005 | o/n | 93.5% | 99.8% |
| 30 | 1200 | CH$_2$Cl$_2$ | 7.6 | Water | 5 | NaHCO$_3$ | 1.005 | o/n | 92.5% | 100% |
| 31 | 75 | CH$_2$Cl$_2$ | 3.68 | Water | 5 | NaHCO$_3$ | 1.005 | o/n | 95.4% | 99.4% |
| 32 | 1194 | CH$_2$Cl$_2$ | 7.6 | Water | 5 | NaHCO$_3$ | 1.005 | o/n | 93.6% | 99.7% |
| 33 | 1400 | CH$_2$Cl$_2$ | 3.8 | Water | 5 | NaHCO$_3$ | 1.005 | o/n | 94.6% | 99.7% |
| 34 | 1600 | CH$_2$Cl$_2$ | 4.6 | Water | 5 | NaHCO$_3$ | 1.005 | o/n | 96.9% | 100% |
| 35 | 100 | CH$_2$Cl$_2$ | 4.6 | Water | 2.5 | NaHCO$_3$ | 1.005 | o/n | 94.7% | 100% |
| 36 | 2000 | CH$_2$Cl$_2$ | 4.6 | Water | 2.5 | NaHCO$_3$ | 1.005 | o/n | 95.2% | 100% |
| 37 | 2104 | CH$_2$Cl$_2$ | 4.6 | Water | 2.5 | NaHCO$_3$ | 1.005 | o/n | 96.8% | 96.9% | o/n = overnight, approximately 16 to 24 hours

It can be seen that high yield and good purity levels were obtained when the primary solvent was selected from tetrahydrofuran and dichloromethane, with particularly high purity obtained with dichloromethane. The best results were obtained using a water co-solvent and a carbonate base.

Example 2: Preparation of Intermediate e

The starting material c prepared in Example 1 was then used to prepare an intermediate e in the preparation of octane-boosting fuel additive f.

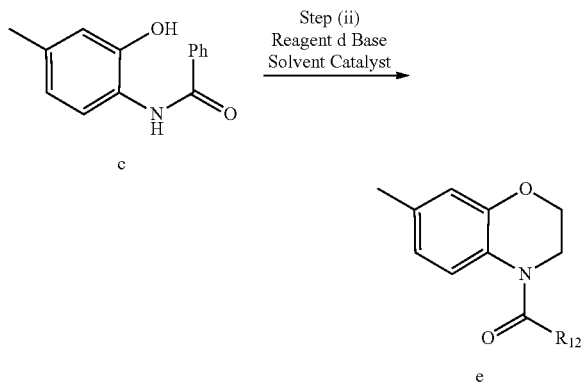

In a fourth experiment, starting material c (1000.0 g; 4400 mmol), dibromoethane (4 eq) and acetonitrile (9000 ml) were added to a jacketed 10 L reactor and stirred. Granular NaOH (4 eq) was added in one portion using cooling (set at 25° C.) to keep the temperature between 25 to 30° C. After 4 hours the second portion of NaOH (4 eq) was added and the jacket temperature was kept at 25° C. Stirring was continued overnight. HPLC showed 92% intermediate e, so the reaction was stirred for a further 24 hours at 25° C. HPLC showed 93.7% intermediate e. Stirring was stopped and the supernatant liquid removed by siphoning (2 L) and stirred with water (6 L) and the liquid decanted away through a P3 sinter from the slightly sticky looking pink solid that remained in the bottom of the container. 6 L of water added to the container with the pink solid in it and more supernatant (2 L) added and the process repeated until no more material could be siphoned out of the reaction vessel. At this point the pink now more crystalline material was filtered out of the container into a sinter and washed with a little water. The reactor outer jacket was set for 10° C. and 3 L of water was added with vigorous stirring (T rises to 33° C.) and when all the material had come away from the sides this material was then siphoned out of the reactor, filtered and added to the previous batch of intermediate e. Combined material tamped down and washed thoroughly with water (3×1 L) and dried. Intermediate e was obtained as a beige sand-textured solid, at a yield of 983 g (88.2%) and at a purity of 100% (as measured using LCMS, (M+1)). Nb. during filtration the P3 sinter became blocked by a very fine darkish material so it was swapped to a P1 sinter.

In a fifth experiment, a stirred (300 rpm) suspension of intermediate c (750.0 g; 3300 mmol) in acetonitrile (7500 ml) was warmed to 22° C. in a 10 L jacketed reactor. 1,2-dibromoethane (4 eq) was added followed by granular NaOH (4 eq) causing the temperature to rise to 29.1° C. before cooling back to 25° C. at which point the jacket was set to 25° C. At this point the reaction mixture was green with a small amount of solids visible. 4 hours after addition of the base, TLC showed approximately 1:1 starter/product with no sign of dimer by-product. The remaining NaOH (4 eq) added in one portion causing the temperature to rise to 26.1° C. before falling back to 25° C. After approximately 30 minutes, the precipitate became heavier although it was still moving around the bottom of the vessel. The reaction mixture was stirred at 25° C. overnight. 24 hours after the start of the reaction, the reaction vessel was still being stirred, albeit with a lot of the precipitate stationary at the bottom of the vessel and the reaction mixture light brown in colour. LCMS showed 95.6% intermediate e with no other impurity above 1.7% and TLC showed no dimer by-product formation. Stirring was stopped and the reaction mixture allowed to settle for 1 hour. The supernatant was siphoned off and diluted with water (3:1 water/supernatant) in batches.

Each time the excess liquid was carefully poured away from the product which was a pinkish oily residue at the bottom of the container. The jacket cooling system of the reactor was set to 10° C. and, with stirring at 300 rpm, 4 L of cold water was added to the reactor (maximum temperature reached: 23° C.) and stirred for 45 minutes at which point all the solid had come away from the reaction vessel and a suspension of solid in the aqueous mixture was seen. This material was siphoned out of the reactor and added to the bucket containing the first batch of material to give approximately 5 to 6 L of aqueous material containing intermediate e. This was then filtered through a P1 sinter and tamped down before washing through with water (2 L). After being sucked partially dry for 1 hour, the material was placed in a drying tray and left on a warming plate until constant mass was achieved. Intermediate e was obtained as a beige solid, at a yield of 732 g (87.5%) and a purity of 100% (as measured using LCMS, (M+1)). NMR was also consistent with the target structure.

Nb. the reaction temperature was kept above 22° C. due to by-product formation during an earlier run when the initial internal temp was only 11.7° C.

Further experiments were carried out under a variety of conditions in order to optimise the production of intermediate e. The results are provided in the following table (the results from the fourth and fifth experiments included at the end of the table):

| | Reagent d | Base | Solvent | Other | Conditions | Result* intermediate e | dimer |
|---|---|---|---|---|---|---|---|
| 1 | DBE 4 eq | K₂CO₃ 4 eq | MIBK | — | reflux 48 hours | 46% | 46% |
| 2 | DBE 2 eq | K₂CO₃ 4 eq | MIBK | — | reflux 48 hours | 27% | 65% |
| 3 | DBE 8 eq | Cs₂CO₃ 4 eq | MIBK | — | reflux 48 hours | 62% | 33% |
| 4 | DBE 4 eq | K₂CO₃ 4 eq | MeCN | — | c added portion-wise over 6 hours, reflux 48 hours (total time) | 54% | 44% |
| 5 | DBE 8 eq | K₂CO₃ 4 eq | MeCN | — | reflux 24 hours | 75% | 25% |
| 6 | DBE 8 eq | K₂CO₃ 4 eq | MeCN | TBAI | reflux 24 hours | 55% | 28% |
| 7 | DBE 8 eq | Cs₂CO₃ 4 eq | MeCN | — | reflux 66 hours | 81% | 18% |
| 8 | DCE 4 eq | K₂CO₃ 4 eq | MeCN | — | reflux 4 hours | Only dimer formed | |
| 9 | Cl-CH₂CH₂-Br 1.25 eq | K₂CO₃ 4 eq | MIBK | — | reflux 24 hours | 38% | 15% |
| 10 | DBE 4 eq | DBU 4 eq | MIBK | — | 24 hrs room temperature then reflux 24 hours | TLC: mostly starter and dimer, a little product and mono-alkylated | |
| 11 | DBE 4 eq | NaH 2.1 eq | DMF | — | Room temperature then slight heating | TLC: mostly starter, mono-alkylated, small amount of product | |
| 12 | ethylene carbonate | CsCO₃ 4 eq | ethylene carbonate | — | 125° C. 1 hour. | TLC: complete degradation | |
| 13 | ethylene carbonate | NaOH 4 eq | | — | 100° C. 3 hours. | Complete conversion to alkylated phenol, no cyclisation | |
| 14 | ethylene carbonate | | ethylene carbonate | dried zeolite Y, sodium (faujasite) | 100° C. 1 hour, then 145° C. 3 hours. | Complete conversion to alkylated phenol, no cyclisation | |
| 15 | DCE 4 eq | NaOH 4 eq | MeCN | — | 30° C. 3 days | Mostly starter, very small amount of product. | |
| 16 | DCE 4 eq | NaOH 4 eq | MeCN | TBAB | 70° C. 20 hours | TLC: many spots | |
| 17 | DCE 4 eq | Cs₂CO₃ 4 eq | MeCN | TBAB | 70° C. 20 hours | 90% | 7% |
| 18 | DCE 8 eq | Cs₂CO₃ 4 eq | MeCN | TBAB | 70° C. 20 hours | 90% | 7% |
| 19 | DCE 8 eq | K₂CO₃ 4 eq | MeCN | TBAB | 70° C. 66 hours | 65% | 34% |
| 20 | DCE 8 eq | Cs₂CO₃ 4 eq | MeCN | TBAB | 70° C. 20 hours, gases trapped in CDCl₃ | 88% | 6% |
| 21 | DIE 1.15 eq | NaOH 4 eq | MeCN | — | Room temperature 2 hours | TLC: complex mixture | |
| 22 | DIE 4 eq | Cs₂CO₃ 4 eq | MeCN | — | Room temperature 2 hours | TLC: complex mixture | |
| 4ᵗʰ | DBE 4 eq | NaOH 8 eq | MeCN | — | 25° C. 48 hours, base added in portions | 87.5% | 0% |
| 5ᵗʰ | DBE 4 eq | NaOH 8 eq | MeCN | — | 25° C. 24 hours, base added in portions | 87.5% | 0% |

*LCMS unless stated otherwise

It can be seen that the use of a sodium hydroxide base, particularly when added to starting material c in portions, encouraged the formation of intermediate e in a good yield and, in some cases, eliminated the formation of the dimer by-product.

It can be seen that the use of a carbonate base, particularly caesium carbonate, also encouraged the formation of intermediate e in a good yield and reduced the formation of the dimer by-product.

The best results were obtained using a solvent selected from methyl isobutyl ketone and acetonitrile, particularly acetonitrile, and where reagent d contains two Br leaving groups or where reagent d contains two Cl leaving groups and a tetrabutylammonium bromide catalyst is used.

Example 3: Preparation of Octane-Boosting Fuel Additive f

In a sixth experiment, a stirred mixture of intermediate e (200 g) and sodium hydroxide (158 g; 5 eq), in water (1 L), under $N_2$, was heated under reflux for 25.5 hours giving a thin oily emulsion. The reaction mixture was cooled to room temperature and the additive f extracted with cyclohexane (3×400 ml). The combined extracts were stirred with charcoal (10 g) and $MgSO_4$ (11 g) for 15 minutes then filtered through a celite pad which was washed with cyclohexane (2×100 ml). The solvents were evaporated to give additive f as a red oil, at a yield of 116.5 g (98.9%) and a purity of 99.1% (as measured using LCMS). NMR was consistent with the target structure.

In a seventh experiment, a stirred mixture of intermediate e (including 8% of the dimer by-product) (50.3 g) and sodium hydroxide (40 g; ~5 eq), in water (250 ml) was heated under reflux for 42 hours giving a thin oily emulsion with a suspended solid (the dimer by-product). The reaction mixture was cooled to room temperature and filtered (sinter grade 2) with washing with water (2×20 ml). The additive was extracted using a procedure similar to that described in connection with the sixth experiment. Fuel additive f was distilled as a red oil, at a yield of 20.4 g and at a purity of 95% with 2% of the dimer by-product present (as measured using LCMS). NMR was consistent with the target structure. The red oil was stirred in hexane (300 ml), decanted from the residual oil and evaporated. Fuel additive f was obtained with a yield of 18.9 g (64%) and at a purity of 100% (as measured using LCMS). NMR was consistent with the target structure.

In an eighth experiment, a stirred mixture of intermediate e (200 g), 5N sodium hydroxide solution (790 ml; 5 eq) and water (315 ml), was heated under reflux for 27 hours giving a thin oily emulsion. The mixture was cooled to room temperature. The process was repeated six times. The mixtures were combined in 3 batches and the product in each extracted using a procedure similar to that described in connection with the sixth experiment. Fuel additive f was obtained as a red oil with a yield of 686.8 g (97.2%) and at a purity of 98.1% (as measured using LCMS). NMR consistent with the target structure.

In a ninth experiment, a stirred suspension of intermediate e (200 g) in 28% HCl (660 ml) and water (340 ml) was heated under reflux for 20 hours, giving a clear solution. The reaction mixture was cooled to room temperature, and NaOH (350 g) in water (800 ml) added over 10 minutes to the solid with cooling keeping the temperature lower than 45° C. The product was extracted using a procedure similar to that described in connection with the sixth experiment. Fuel additive f was obtained as a brown oil with a yield of 112.0 g (95%) and at a purity of 99.9% (as measured using LCMS). NMR was consistent with the target structure.

In a tenth experiment, a stirred suspension of intermediate e (200 g) in 28% HCl (500 ml) and water (500 ml) was heated under reflux for 30 hours, giving a clear solution. The reaction mixture was cooled to room temperature (o/n) and 5N NaOH solution (1.1 L) added over 5 minutes to the solid. The oily solution was extracted using a procedure similar to that described in connection with the sixth experiment. Fuel additive f was obtained as a yellow oil with a yield of 112.7 g (95.7%) and at a purity of 99.5% (as measured using LCMS). NMR was consistent with the target structure.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope and spirit of this invention.

The invention claimed is:

1. A method for preparing a fuel additive having the formula:

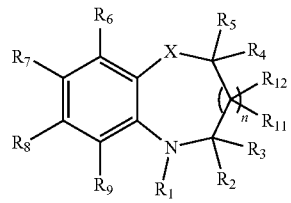

where: $R_1$ is hydrogen;

$R_2$, $R_3$, $R_4$, $R_5$, $R_{11}$ and $R_{12}$ are each independently selected from hydrogen, alkyl, alkoxy, alkoxy-alkyl, secondary amine and tertiary amine groups;

$R_6$, $R_7$, $R_8$ and $R_9$ are each independently selected from hydrogen, alkyl, alkoxy, alkoxy-alkyl, secondary amine and tertiary amine groups;

X is selected from —O— or —NR$_{10}$—, where R$_{10}$ is selected from hydrogen and alkyl groups; and n is 0 or 1, said method comprising carrying out the following reaction:

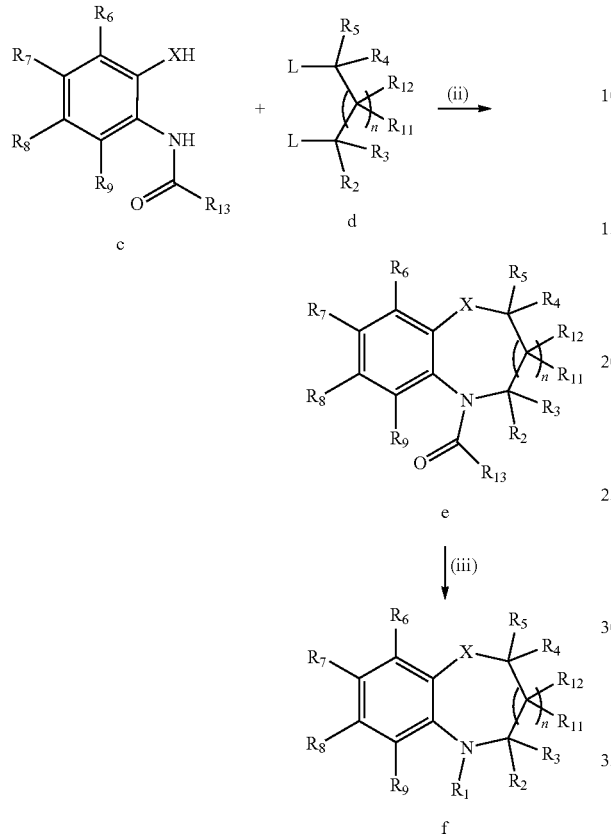

where: R$_{13}$ is selected from alkyl and aryl groups; and
each L is independently selected from leaving groups, and wherein step (ii) is conducted in the presence of a base selected from alkali metal hydroxides and alkali metal carbonates, and wherein the base is used in an amount of at least 2 molar equivalents as compared to starting material c.

2. A method according to claim 1, wherein the alkali metal hydroxide is selected from sodium hydroxide and potassium hydroxide, and wherein the alkali metal carbonate is selected from sodium carbonate, potassium carbonate, sodium bicarbonate, potassium bicarbonate and caesium carbonate.

3. A method according to claim 1, wherein the base is selected from alkali metal hydroxides.

4. A method according to claim 1, wherein the base is used in an amount of from 2 to 12 molar equivalents as compared to starting material c.

5. A method according to claim 1, wherein the base is added to the starting material c in at least two portions, and wherein no more than 70% of the total amount of base used is added in each portion.

6. A method according to claim 1, wherein reagent d is used in an amount of from 1 to 20 molar equivalents as compared to starting material c.

7. A method according to claim 1, wherein step (ii) is conducted in the presence of a solvent selected from methyl isobutyl ketone and acetonitrile.

8. A method according to claim 1, wherein step (ii) is conducted in the presence of a catalyst.

9. A method according to claim 1, wherein step (iii) is carried out in an aqueous solution.

10. A method according to claim 1, wherein R$_{13}$ is selected from methyl, ethyl and phenyl.

11. A method according to claim 1, wherein each L is independently selected from: halides, substituted aryloxy groups, and sulfonates.

12. A method for preparing a starting material c for use in claim 1, said method comprising carrying out the following reaction:

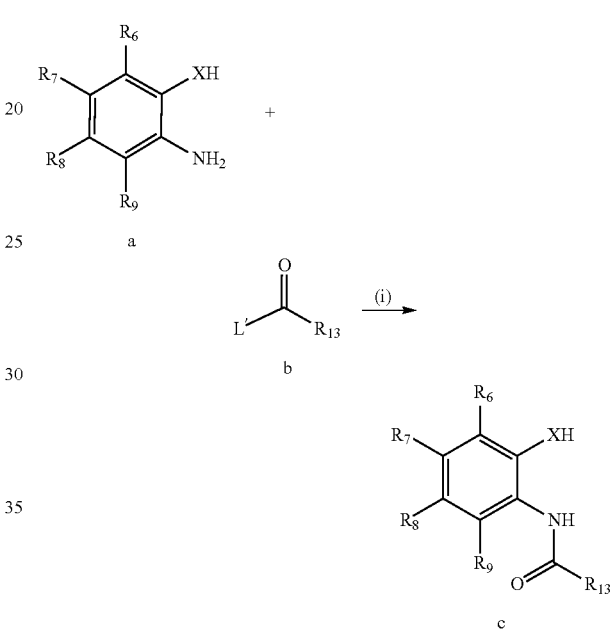

where: L' is a leaving group, and wherein step (i) is carried out in the presence of a solvent system which comprises a primary solvent, the primary solvent selected from tetrahydrofuran and dichloromethane.

13. A method according to claim 12, wherein at least 90% by volume of the solvent system is made up of the primary solvent and, if present, water.

14. A method according to claim 12, wherein the primary solvent is dichloromethane.

15. A method according to claim 12, wherein the solvent system is used in an amount of from 5 to 15 ml/g of reagent a.

16. A method according to claim 12, wherein the reagent b is used in an amount of from 1 to 1.05 molar equivalents as compared to reagent a.

17. A method according to claim 12, wherein step (1) is conducted in the in the presence of a base.

18. A process for preparing a fuel for a spark-ignition internal combustion engine, said process comprising:
preparing a fuel additive using a method according to claim 1; and
blending the fuel additive with a base fuel.

* * * * *